United States Patent
Moriyama

(10) Patent No.: US 7,285,253 B2
(45) Date of Patent: *Oct. 23, 2007

(54) VESSEL FOR HIGH-TEMPERATURE HIGH-PRESSURE STEAM STERILIZATION

(75) Inventor: Hiroki Moriyama, Akishima (JP)

(73) Assignee: Olympus Corporation, Tokyo (JP)

( * ) Notice: Subject to any disclaimer, the term of this patent is extended or adjusted under 35 U.S.C. 154(b) by 669 days.

This patent is subject to a terminal disclaimer.

(21) Appl. No.: 09/894,659

(22) Filed: Jun. 28, 2001

(65) Prior Publication Data

US 2002/0001551 A1    Jan. 3, 2002

(30) Foreign Application Priority Data

Jun. 30, 2000    (JP)    ............... 2000-199741

(51) Int. Cl.
*A61L 2/00*    (2006.01)

(52) U.S. Cl. .............. 422/297; 134/170; 422/292; 422/300; 422/301

(58) Field of Classification Search ............... 422/292, 422/294, 297, 300, 301; 134/170
See application file for complete search history.

(56) References Cited

U.S. PATENT DOCUMENTS

| | | | |
|---|---|---|---|
| 3,633,758 A * | 1/1972 | Morse et al. ............ 211/85.13 |
| 4,730,729 A * | 3/1988 | Monch ..................... 206/370 |
| 4,798,292 A * | 1/1989 | Hauze ...................... 206/439 |
| 5,288,467 A * | 2/1994 | Biermaier .................. 422/116 |
| 5,534,221 A * | 7/1996 | Hillebrenner et al. ......... 422/33 |
| 5,759,490 A * | 6/1998 | Malchesky .................. 422/28 |
| 5,843,387 A * | 12/1998 | Dane et al. ................ 422/300 |
| 5,882,589 A * | 3/1999 | Mariotti .................... 422/28 |
| 6,361,751 B1 * | 3/2002 | Hight, III .................. 422/292 |

FOREIGN PATENT DOCUMENTS

| EP | 271157 | * | 6/1988 |
|---|---|---|---|
| JP | H5-285103 | | 11/1993 |
| JP | 2000-060791 | | 2/2000 |

* cited by examiner

Primary Examiner—Krisanne Jastrzab
(74) Attorney, Agent, or Firm—Scully, Scott, Murphy & Presser, P.C.

(57) ABSTRACT

The vessel for high-temperature high-pressure steam sterilization is a vessel for accommodating at least an endoscope and performing high-temperature high-pressure steam sterilization, including: an accommodating recess section for accommodating an elongated and thin insertion part of the endoscope having a flexible section; and pressing force preventing schemes for preventing local pressing forces from being applied to the outer surface of the flexible section when accommodated in the accommodating recess section.

11 Claims, 7 Drawing Sheets

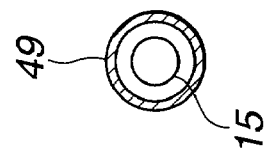
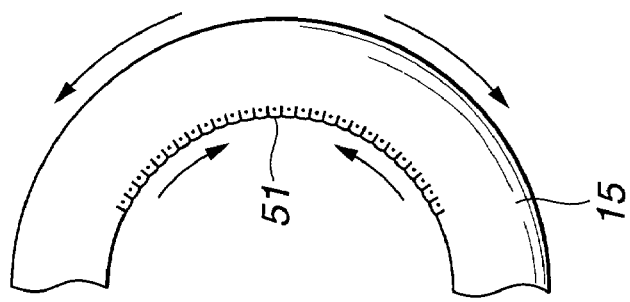
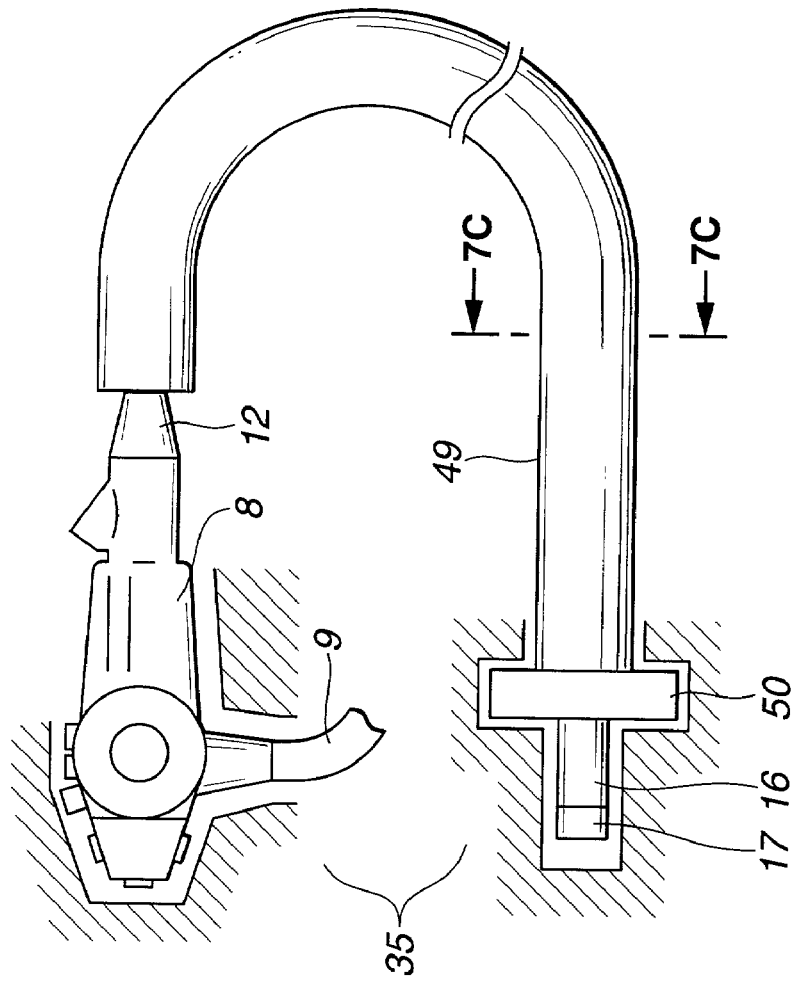

VESSEL FOR HIGH-TEMPERATURE HIGH-PRESSURE STEAM STERILIZATION

This application claims benefit of Japanese Application No. 2000-199741 filed in Japan on Jun. 30, 2000, the contents of which are incorporated by this reference.

BACKGROUND OF THE INVENTION

1. Field of the Invention

The present invention relates to a vessel for high-temperature, high-pressure steam sterilization, whereby autoclave sterilization (high-temperature, high-pressure steam sterilization) can be conducted in an unhindered manner.

2. Description of the Related Art

At present, in the medical field, there is wide use of endoscopes whereby surgical procedures can be performed by inserting an elongated and thin insertion part into a body cavity, for example, to inspect the recesses of a body cavity, for example, or in order to use a surgical tool, if required.

In using medical endoscope devices of this kind, it is absolutely imperative that the endoscope being used is reliably disinfected and sterilised.

In recent years, wide use has been made of autoclave sterilization (high-temperature, high-pressure steam sterilization) as a method for sterilizing endoscopes, which does not involve complex tasks, provides endoscopes for use promptly after sterilization, and which also has low running costs.

In a known autoclave sterilization method of this kind, as described in Japanese Unexamined Patent Publication No.H5-285103, endoscopes which can be subject to high-temperature high-pressure steam sterilization are placed inside an autoclave sterilizing device.

Known representative conditions for autoclave sterilization are described in U.S. Standards ANSI/AAMI ST37-1992 published by the American Association of Medical Instruments, under the approval of the American Standards Association. These conditions specify sterilization processing for 4 minutes at 132° C. for pre-vacuum type sterilization and sterilization processing for 10 minutes at 132° C. for gravity type sterilization.

The environmental conditions in autoclave sterilization are extremely harsh for the precision electronic equipment, namely, the electronic microscope device, which is equipped with an imaging device, such as CCDs, or the like, and various countermeasures must be taken in order to achieve an electronic endoscope having resistance to an environment of this kind, for instance, high-pressure countermeasures, high-temperature countermeasures, steam countermeasures, and the like, compared to an endoscope which is used only with other disinfection and sterilization means.

More particularly, since the insertion part of the endoscope is inserted inside a patient, it is required to have various subtle characteristics, such as flexibility, elasticity, and the like, and therefore, there is a tendency for this part to be more vulnerable to high pressure, high temperature and steam, in other words, more liable to decline in characteristics, than the rigid front part, and hence it requires more advanced countermeasures.

Moreover, when performing autoclave sterilization, in addition to the endoscope, various buttons for controlling ventilation and water supply, and the like, removed from the endoscope, the waterproof cap, or an instrument, such as forceps, attached to the endoscope, are placed together on a tray and introduced into the autoclave sterilization device.

In this case, if autoclave sterilization is performed whilst one of the aforementioned peripheral elements of the endoscope, for example, an instrument, such as forceps, is overlapping or contacting the insertion part of the endoscope, or an elastic part thereof, such as the universal cord, or the like, then there is a risk that this part will be pressed by the aforementioned instrument, thereby damaging the insertion part of the endoscope.

It is important to design not only the composition of the insertion part of the endoscope itself, but also the mode by which elements are inserted into the autoclave sterilization device, in such a manner that the insertion part of the endoscope is not damaged by peripheral parts of the endoscope.

However, in the prior art, endoscopes which can be subjected to high-temperature high-pressure steam sterilization have been provided with high-temperature countermeasures when introduced into autoclave sterilization devices, but no consideration has been given to protecting the insertion part of the endoscope from peripheral parts contacting and pressing against same.

OBJECTS AND SUMMARY OF THE INVENTION

It is a first object of the present invention to provide a vessel for high-temperature high-pressure steam sterilization whereby no damage is caused to the insertion part of the endoscope when an endoscope capable of undergoing high-temperature high-pressure steam sterilization is subjected to autoclave sterilization.

It is a second object of the present invention to provide a vessel for high-temperature high-pressure steam sterilization whereby deformation after autoclave sterilization can be reduced.

Briefly, the vessel for high-temperature high-pressure steam sterilization according to the present invention is a vessel for accommodating at least an endoscope, and performing high-temperature high-pressure steam sterilization, comprising: an accommodating recess section for accommodating an elongated and thin insertion part of the endoscope, which comprises a flexible section; and pressing force preventing means for preventing local pressing forces from being applied to the outer surface of the flexible section accommodated in the accommodating recess section.

The above and other objects, features and advantages of the invention will become more apparent from the following description when taken in conjunction with the accompanying drawings.

BRIEF DESCRIPTION OF THE DRAWINGS

FIG. 7A is a sectional diagram showing a portion of a vessel for high-temperature high-pressure steam sterilization and the insertion part of an endoscope, in a case where the insertion part of the endoscope has been accommodated in a vessel for high-temperature high-pressure steam sterilization according to a third embodiment of the present invention;

FIG. 7B is a diagram showing a portion of the insertion part of the endoscope, in a case where the insertion part of the endoscope has been accommodated in a vessel for high-temperature high-pressure steam sterilization according to a third embodiment of the present invention;

FIG. 7C is a diagram showing a portion of the insertion part of the endoscope, in a case where the insertion part of the endoscope has been accommodated in a vessel for high-temperature high-pressure steam sterilization according to a third embodiment of the present invention;

DESCRIPTION OF THE PREFERRED EMBODIMENTS

Figure 1:
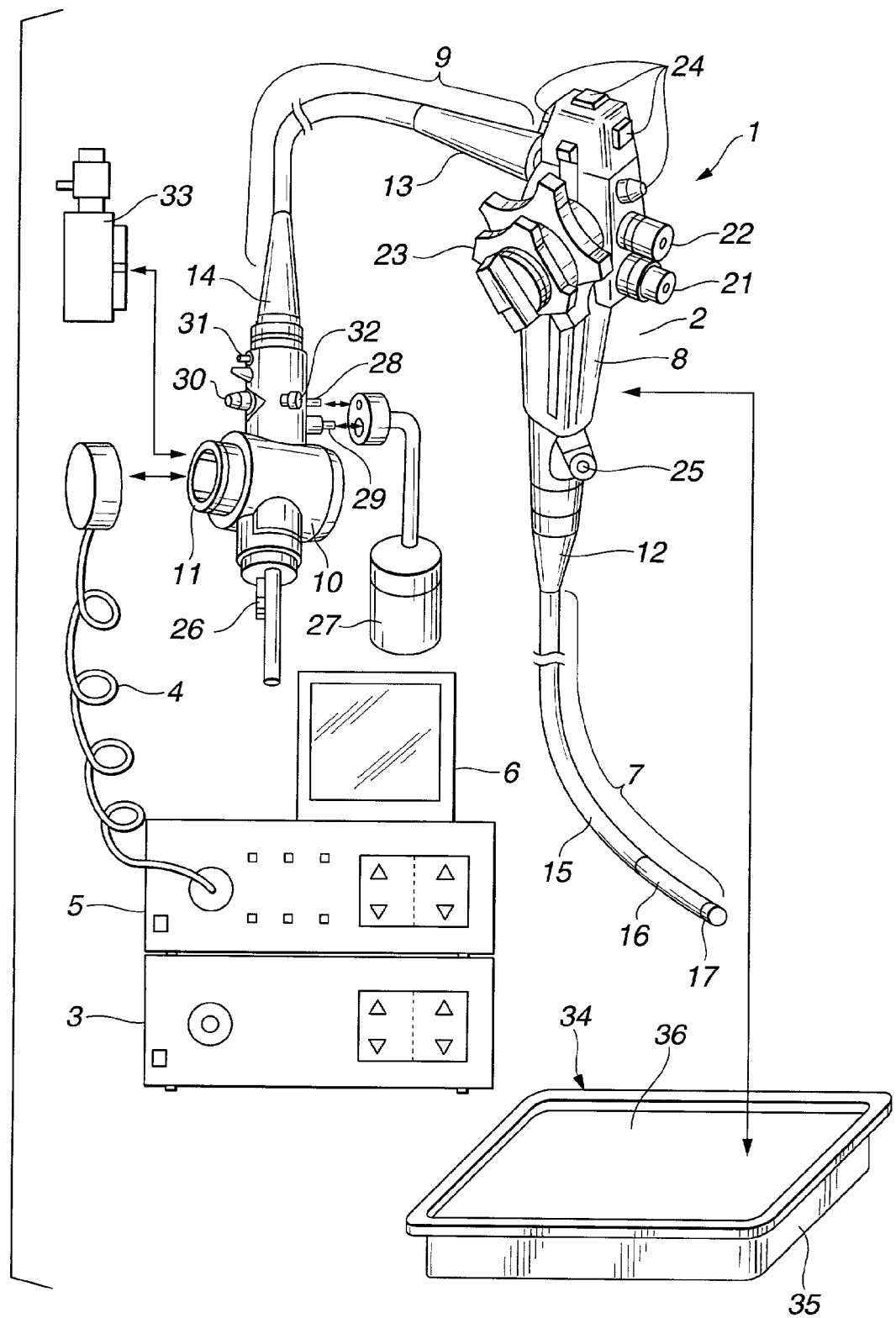
FIG. 1 is a diagram showing the general composition of an endoscope device using a vessel for high-temperature high-pressure steam sterilization according to a first embodiment of the present invention.

Embodiments of the present invention is described below referring to the drawings.

Initially, a first embodiment of the present invention will be described referring to FIG. 1, FIG. 2, FIG. 3, FIG. 4, FIG. 5A and FIG. 5B.

As shown in FIG. 1, an endoscope device 1 used in the vessel for high-temperature high-pressure steam sterilization according to the first embodiment of the present invention comprises: an endoscope 2 having an imaging means (not shown); a light source device 3, which is detachably connected from the endoscope 2 freely, for supplying illuminating light to a light guide provided in the endoscope 2; a video processor 5, which is connected to the endoscope 2 via a signal cable 4, for controlling the imaging means of the endoscope 2 and outputting a standard video signal by processing a signal obtained from the imaging means; and a monitor 6 for inputting the video signal from the video processor 5 and displaying endoscope images.

The aforementioned endoscope 2 is constituted in such a manner that, after being used for observation and/or surgical procedures, it can be rinsed and then sterilized by autoclave sterilization (high-temperature high-pressure steam sterilization).

The endoscope 2 comprises: an elongated and thin insertion part 7 having elasticity; an operating part 8 provided at the base end side of the insertion part 7; a universal cord 9 having elasticity, extending from the side portion of the operating part 8; a connector part 10 provided on the end portion of the universal cord 9 and being detachably connectable from the aforementioned light source device 3 freely; and an electric connector section 11 extending from the side portion of this connection part 10 and being detachably connectable from the aforementioned signal cable 4 which is connectable with the aforementioned video processor 5 freely.

An air ventilation section (not shown) which connects the interior portion and exterior portion of the endoscope 2 is provided in the aforementioned electrical connector part 11.

An insertion part side bend prevention member 12 having an elastic member for preventing severe bending of the connectable part is provided in the connecting portion between the insertion part 7 and the operating section 8.

An operating part side bend prevention member 13 is provided in the connecting portion between the operating part 8 and the universal cord 9.

A connection part side bend prevention member 14 is provided in the connecting portion between the universal cord 9 and the connector part 10.

The insertion part 7 comprises: a flexible tube section 15 forming a non-rigid elastic section having flexibility; a bending section 16 which can be bent by operation of the aforementioned operating section 8 provided on the distal side of the flexible tube section 15; and a distal end section 17 provided on the tip of the insertion part 7, wherein an observation optics system, illumination optics system, and the like, (not shown) are provided.

The aforementioned operating section 8 comprises: ventilation and water supply operating buttons 21 for activating air ventilation and water supply operations; a suction operating button 22 for activating a suction peration; a bend operation knob 23 for activating a bend operation of the bending section 16; a plurality of remote switches 24 for remote controlling of the aforementioned video processor 5, and a surgical instrument inserting aperture 25, that is an opening connecting to the aforementioned surgical instrument channel.

The distal end section 17 comprises: a fluid supply aperture and ventilation and water supply nozzle for injecting cleaning solutions and gases towards the observation window of the observation optics system (not shown), by means of a ventilation operation and water supply operation; and a suction aperture (not shown) provided in the insertion part 7, that is an opening in the distal side of the surgical instrument channel (not shown), for inserting the surgical instrument and sucking up body fluid from the body cavity.

The connector part 10 comprises: a gas supply cap 26, provided internally to the light source device 3, which can be freely connected detachably from a gas supply source (not shown); a water supply tank pressure cap 28 and fluid supply cap 29, which can be freely connected detachably from a water supply tank 27 forming a fluid supply source; a suction cap 30 connected to a suction source (not shown), for performing suction via the suction aperture of the distal end section 17; and an injection cap 31 connected to water supply means (not shown), for providing a water supply via the fluid supply aperture of the distal end section 17.

An earthing terminal cap 32 is provided on the aforementioned connection section 10 in order to return any leakage current to the high-frequency processing device, in the event that a high-frequency leakage current arises in the endoscope when performing a high-frequency procedure, or the like.

A restricting section (not shown) having a shape corresponding to that of the endoscope 2 is formed in the connector part 10. This restricting section is formed in such a manner that respective portions of the endoscope 2 are accommodated in predetermined positions thereof. Furthermore, an insertion part restricting section (not shown) which accommodates the insertion part 7 is provided in the restricting section.

A waterproof cap with pressure adjusting vent (hereinafter, called waterproof cap) 33 is freely connected detachably from the electrical connector part 11, and a pressure adjusting value (not shown) is provided in this waterproof cap 33.

As described above, representative conditions for high-temperature high-pressure steam sterilization, according to U.S. Standards ANSI/AAMI ST37-1992, are sterilization at 132° C. for 4 minutes in pre-vacuum type sterilization, and sterilization at 132° C. for 10 minutes in gravity type sterilization.

The temperature conditions for the sterilization process in autoclave sterilization vary according to the form of the autoclave sterilization device (not shown) and the time period of the sterilization process, but in general, the temperature is set between 115° C. and 138° C.

Some sterilization devices allow the sterilization temperature to be set to approximately 142° C. The time conditions vary depending on the temperature conditions of the sterilization process, but in general, a time of between 3 minutes and 60 minutes is specified. Some types of sterilization devices allow time of the order of 100 minute to be set. The pressure inside the sterilization chamber during processing is generally set to approximately −0.2 MPa with respect to atmospheric pressure.

Autoclave sterilization using a general pre-vacuum process involves a pre-vacuum step wherein the interior of the sterilization chamber accommodating the instrument to be sterilized is reduced to a vacuum state before the sterilization process; and following this, a sterilization step wherein sterilization is performed by introducing high-pressure, high-temperature steam into the sterilization chamber.

The former step, the pre-vacuum step, serves to allow the steam to impregnate into the most detailed portions of the instrument being sterilised during the subsequent sterilization process, and by reducing the sterilization chamber to a vacuum, the high-pressure high-temperature steam is caused to pass over the entirety of the instrument being sterilized.

The pressure of the sterilization chamber in the pre-vacuum process is generally set to −0.07 MPa −0.09 MPa with respect to the atmospheric pressure.

Furthermore, in order to dry the instrument being sterilized after sterilization, a pre-vacuum type autoclave sterilization process also includes a drying step wherein the interior of the sterilization chamber is reduced to a vacuum again, after the aforementioned sterilization step.

In this drying step, the steam is expelled from the sterilization chamber by reducing the interior of the sterilization chamber to a vacuum, thereby promoting drying of the object being sterilized inside the sterilization chamber. The pressure inside the sterilization chamber during this step is generally set to −0.07 MPa-0.09 MPa with respect to the atmospheric pressure.

When performing autoclave sterilization of the aforementioned endoscope 2, sterilization is performed with the aforementioned waterproof cap 33 with pressure adjusting vent in an installed state on the electric connector section 11. In this state, the pressure adjusting value (not shown) of the waterproof cap 33 is closed, the ventilation aperture is sealed by the waterproof cap 33, and hence the interior of the endoscope 2 is hermetically sealed and waterproofed with respect to the exterior.

In the case of a sterilization method having the aforementioned pre-vacuum step, as the pressure inside the sterilization chamber is reduced during the pre-vacuum step and a pressure differential is generated by the fact that the external pressure is lower than the internal pressure of the endoscope 2, the aforementioned pressure adjusting vent opens, the interior and exterior of the endoscope 2 are connected by means of the air ventilation aperture, and hence a large pressure differential is prevented from occurring between the interior of the endoscope 2 and the interior of the sterilization chamber. By this means, the endoscope 2 is prevented from being damaged by the pressure difference between the interior and exterior thereof.

In the aforementioned sterilization process, if the pressure inside the sterilization chamber is increased and a pressure differential arises wherein the pressure at the exterior of the endoscope 2 is greater than the internal pressure thereof, then the aforementioned pressure adjusting vent closes. Thereby, the high-pressure high-temperature steam does not enter directly inside the endoscope 2 by means of the waterproof cap 33 and the ventilation aperture.

However, the high-temperature high-pressure steam does gradually penetrate inside the endoscope 2 via the outer skin of the flexible tube section 15 which is made from a polymer material, or the O ring made from fluoro rubber or silicon rubber which forms sealing means provided at the connecting section between the endoscope 2 and the outer body thereof. Moreover, the outer body of the endoscope 2 assumes a state where a pressure acting from the exterior to the interior of the device is generated equalling the sum of the pressure reduced in the pre-vacuum step, plus the pressure applied in the sterilization step.

In the case of a method which includes a vacuum step after the sterilization process, then virtually simultaneously with the occurrence of a pressure differential caused by the external pressure of the endoscope 2 being lower than the internal pressure thereof, as the pressure of the sterilization chamber is reduced in the vacuum step, the aforementioned pressure adjusting vent will open, thereby connecting the interior and exterior of the endoscope 2 via the ventilation aperture, and hence preventing the occurrence of a large pressure differential between the interior of the endoscope 2 and the interior of the sterilization chamber. By this means, the endoscope 2 is prevented from being damaged by the differential between the internal and external pressures thereof.

When this vacuum step has finished, and the pressure of the interior of the sterilization chamber is raised, a pressure differential arises wherein the external pressure of the endoscope 2 is greater than the internal pressure thereof, and hence the pressure adjusting vent closes.

As described above, when all of the steps in the high-temperature, high-pressure steam sterilization process have completed, there remains a state where an external pressure acting towards the interior is exerted, according to the amount of vacuum applied to the outer body of the endoscope 2 in the aforementioned vacuum step.

When the waterproof cap 33 is removed from the electric connector section 11, the interior and exterior of the endoscope 2 are connected via the ventilation aperture, and the interior of the endoscope 2 assumes atmospheric pressure, thereby removing the load created by the pressure generated on the outer body of the endoscope 2.

In this embodiment, the aforementioned endoscope 2 is accommodated in a sterilization accommodating case 34 forming a vessel for high-temperature high-pressure steam sterilization, and autoclave sterilization is performed by introducing this sterilization accommodating case 34 into an autoclave sterilization device (not shown).

The accommodating case 34 comprises a tray 35 formed with an accommodating recess (described hereinafter) for accommodating the insertion part of the endoscope, and a rear cover member 36 provided on the tray 35. A plurality of ventilation holes (not shown) are provided in the tray 35 and rear cover member 36, in such a manner that steam is able to pass through these holes during autoclave sterilization.

Figure 2:
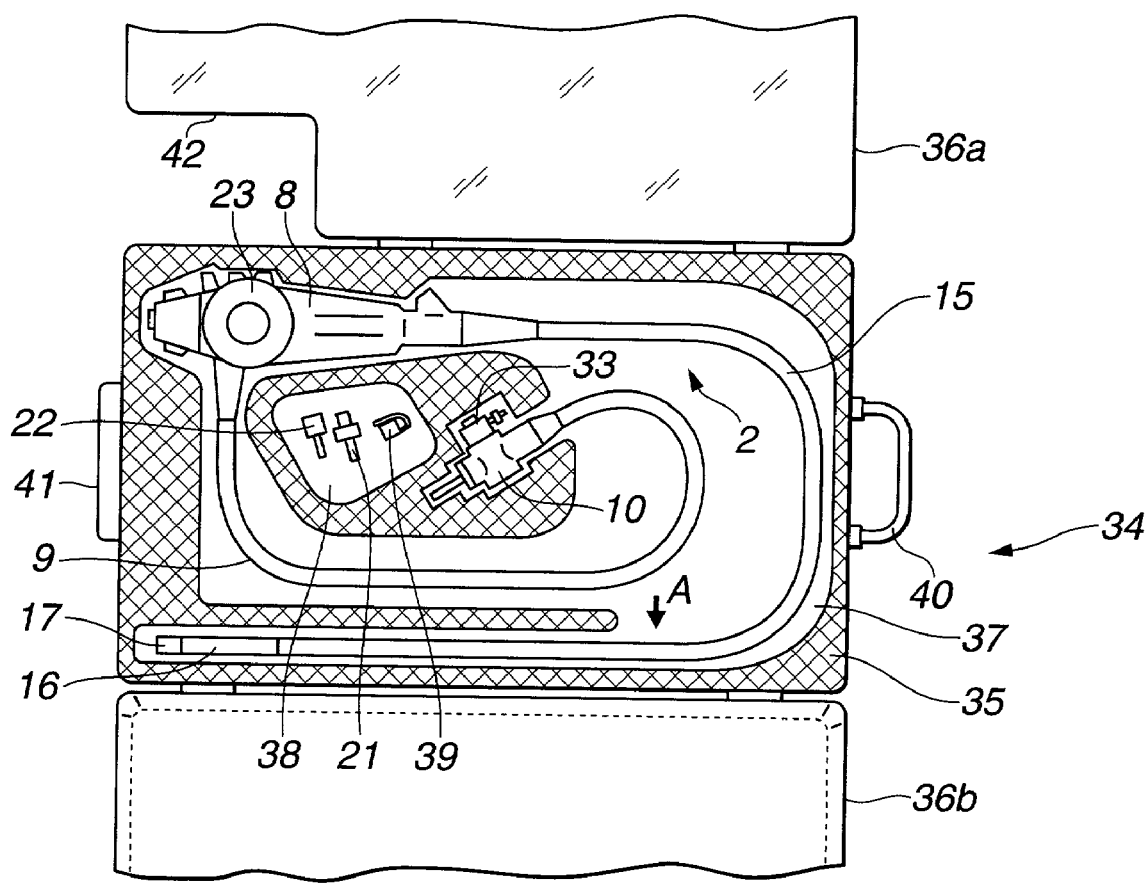
FIG. 2 is a plan view of a state where an endoscope is accommodated in the vessel for high-temperature high-pressure steam sterilization according to the first embodiment, showing the vessel for high-temperature high-pressure steam sterilization in a state where both a middle lid and outer lid are opened.

FIG. 2 shows a situation where the aforementioned endoscope 2 is accommodated in the sterilization accommodating case 34 prior to introduction into the autoclave sterilization device.

As shown in FIG. 2, an endoscope accommodating section 37, being an accommodating recess section for accommodating the endoscope 2, is formed in the tray 35, and the under face and side faces of this endoscope accommodating section 37 are formed as virtually flat faces.

When the endoscope 2 is accommodated in the endoscope accommodating section 37 with a certain amount of clearance, the operating section 8 of the endoscope 2 accommodated therein is not slid widely, and the accommodated shape (bending shape) of the universal cord 9 and the flexible tube section 15 are determined automatically.

In FIG. 2, the portion indicated by the hatching projects beyond the endoscope accommodating section 37, and the height of this hatched section is higher than the operating section 8 or the connector section 10, but it is lower than the maximum possible height of the bend operating knob 23. Furthermore, since the flexible tube section 15, universal cord 9, operating section 8 and connector section 10 have lower height (narrower width), then even when these elements are accommodated in the endoscope accommodating section 37, they are sufficiently lower than the aforementioned hatched section.

In the portion where the connector part 10 is accommodated, a small accommodating section 38 is formed for accommodating small items, such as the ventilation and water supply buttons 21, or suction operation button 22, removed from the endoscope 2, or a surgical instrument shaft 39 which is attached to the surgical instrument insertion aperture 25 during medical investigation, thereby enabling autoclave sterilization.

As shown in the figure, the shape of the portion of the endoscope accommodating section 37 accommodating the operating section 8 is provided within only a small clearance, in order that the endoscope 2 cannot be accommodated inside the endoscope accommodating section 37 whilst the aforementioned ventilation and water buttons 21, suction operation button 22 and surgical instrument shaft 39 are attached to the endoscope 2.

Consequently, the endoscope 2 can only be accommodated in the endoscope accommodating section 37 once the ventilation and water supply operating buttons 21, suction operating button 22 and surgical instrument shaft 39 have been removed from the endoscope 2. Moreover, the removed ventilation and water supply operating buttons 21, suction operating button 22 and surgical instrument shaft 39 can be accommodated in the aforementioned small accommodating section 38. In this way, by accommodating the endoscope 2, the ventilation and water supply operating buttons 21, the suction operating button 22 and the surgical instrument shaft 39 inside the sterilization accommodating case 34, it is possible to allow the steam to make sufficient contact with the interior of the tube portion of the endoscope 2, and the connecting portions between the endoscope 2 and the ventilation and water supply operating buttons 21, suction operating button 22 and surgical instrument shaft 39, during high-temperature high-pressure steam sterilization.

An endoscope 2 may have a short or a long flexible tube section 15. In devices having the long flexible tube section 15, it may be arranged in a circular fashion, as shown in FIG. 2. In the present case, the aforementioned flexible tube section 15 is constituted in such a manner it can be accommodated and positioned in an approximately straight shape, from the portion indicated by arrow A. The reason for this is as follows.

In the case of an endoscope used in the lower digestive tract, the insertion part is between 133 system and 168 cm. In general, it can be considered that when this is inserted from the anus of the colon until the appendix, whilst eliminating superfluous bending as far as possible, approximately 70 cm is inserted, and therefore the portion up to 70 cm is the most important portion which will be inserted in practically all patients. Consequently, in the present embodiment, this portion in particular is accommodated in an approximately straight shape, in such a manner that it does not contain any kinks, or the like, during the high-temperature high-pressure steam sterilization process.

As described above, the aforementioned lid member 36 is provided in the aforementioned sterilization accommodating case 34 with respect to the aforementioned tray 35, and this lid member 36 is constituted by providing two lid members—a middle lid 36a and an outer lid 36b.

FIG. 2 shows the middle lid 36a and the outer lid 36b in an opened state.

These two lid members, the middle lid 36a and outer lid 36b, are constituted in such a manner that the outer lid 36b closes from above after the middle lid 36a has been closed against the tray 35, but not vice versa. The middle lid 36a is a planar member in which a cutaway section 42 is formed in a portion thereof in such a manner that that only the bend operating knob 23 of the aforementioned operating section 8 can project therethrough. The colour of the middle lid 36a is transparent, in such a manner that the whole structure of the accommodated endoscope 2 is visible. It does not matter if the colour of the middle lid 36a is not transparent.

The tray 35 is provided with a knob 40 for gripping firmly in the vertical direction when carrying same, and in addition to the knob 40, in order that the tray 35 can be held in a horizontal position also, a knob 41 for holding by a finger, which is provided on the side of the tray 35.

Figure 3:
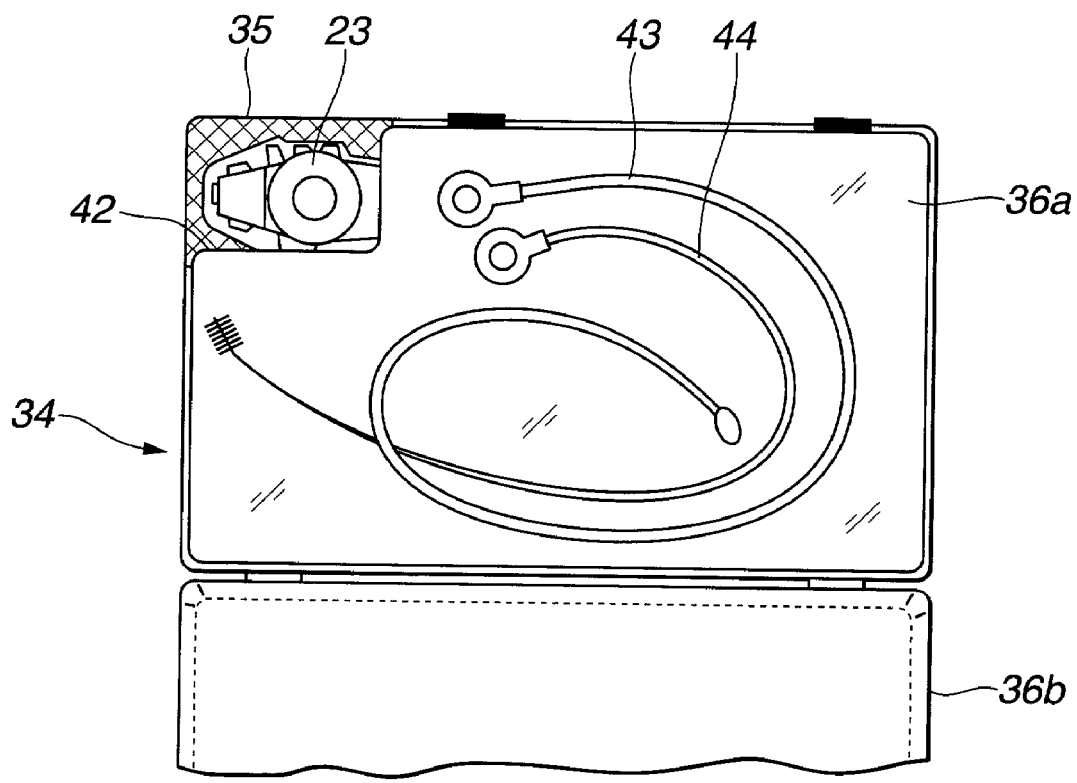
FIG. 3 a plan view of a state where an endoscope is accommodated in the vessel for high-temperature high-pressure steam sterilization according to the first embodiment, showing a situation the middle lid of the vessel for high-temperature high-pressure steam sterilization is closed.

When the middle lid 36a has been closed from the state shown in FIG. 2, the middle lid 36a is closed so as to confront the shaded portion of the tray 35 as shown in FIG. 3, and as described above, only the bend operating knob 23 projects through the aforementioned cutaway section 42. When the middle lid 36a is in a closed state, respective portions of the endoscope 2 (such as the distal end section 17, bendable section 16, flexible tube section 15, operating part 8, universal cord 9, and the like), are positioned and accommodated within the endoscope accommodating section 37, whilst having a predetermined clearance of a certain amount about the entire perimeter thereof, such that they do not contact any elements other than the aforementioned tray 35. Thereby, the endoscope accommodating section 37 formed in the tray 35 is provided with sufficient clearance with respect to the endoscope 2, and since the respective portions of the endoscope 2 are approximately positioned, there is never any overlapping between predetermined portions of the endoscope and other portions thereof.

It is also possible for the surgical instrument 43 and rinsing tool 44 to be placed in a circular fashion on top of the lid member 36 in this state. Although the outer lid 36b is closed thereupon, the surgical instrument 43 and rinsing tool 44 can still be accommodated in the sunken portion of the outer lid 36b.

Accordingly, by providing the aforementioned middle lid 36a, the endoscope 2 accommodated inside the endoscope accommodating section 37 can be separated from peripheral elements other than the endoscope 2, such as the surgical instrument 43 and rinsing tool 44, or the like, when this middle lid 36a is closed against the tray 35, and hence there is no contact between these peripheral elements and any portions of the endoscope 2, in particular, the universal cord 9 or the flexible tube section 15. Consequently, no local pressing forces are applied to the universal cord 9 or the flexible tube section 15. There is a possibility that the aforementioned surgical instrument 43, or rinsing tool 44 will press against the bend operating knob 23, but since the bend operating knob 23 is made from hard resin material, it is not liable to undergo plastic deformation as are the flexible tube section 15 or universal cord 9.

Figure 4:
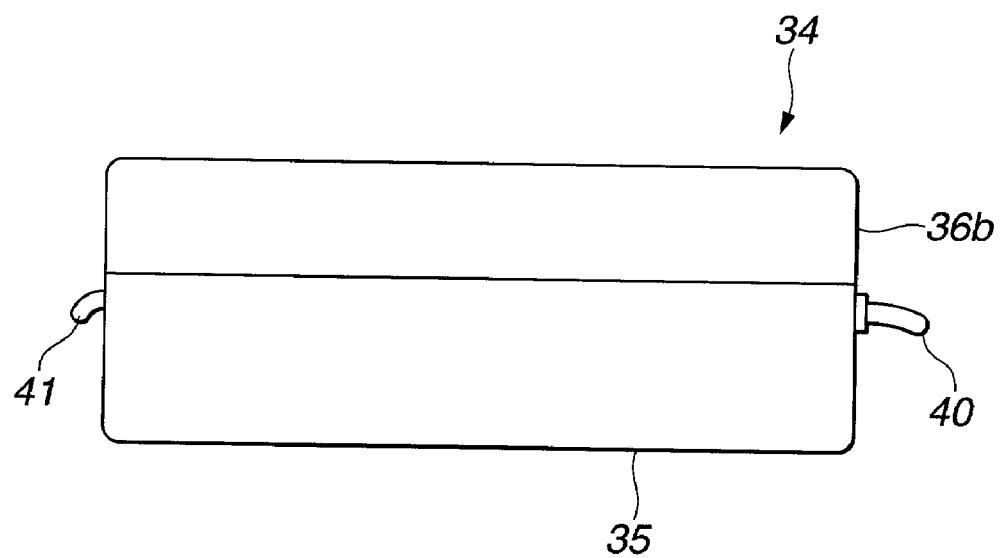
FIG. 4 is an external side view of a state where an endoscope is accommodated in a vessel for high-temperature high-pressure steam sterilization according to the first embodiment, showing a situation where the outer lid of the vessel for high-temperature high-pressure steam sterilization is closed.

Moreover, FIG. 4 shows a state where the outer lid 36b is also closed, from the state shown in FIG. 3.

FIG. 4 shows a side view of the tray 35. Since the elements are not accommodated in a hermetically sealed manner, even when the lids are closed completely in this way, it is possible for steam to reach the 2 in a satisfactory manner.

After an endoscopic examination has been completed, the endoscope and the other members and surgical instruments, removed from the endoscope, are accommodated inside a sterilization accommodating case 34 constituted as described above, introduced into an autoclave sterilization device, and autoclave sterilization is carried out as described above.

Figure 5A:
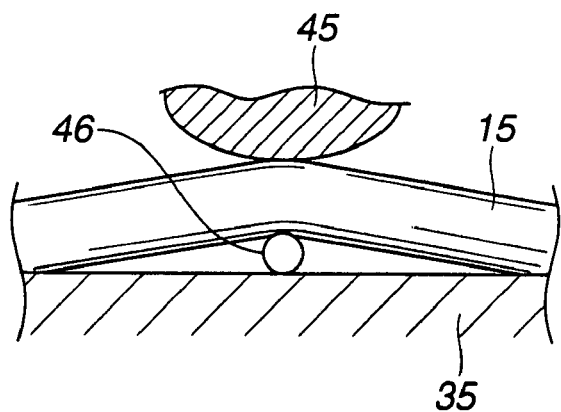
FIG. 5A is a sectional view showing the state of the flexible tube section of an endoscope when an endoscope is accommodated in a sterilization device, according to the prior art.

Conventionally, as shown in FIG. 5A, it has occurred that the peripheral elements 46, such as the surgical instrument 43, rinsing tool 44, or the like, are placed under the flexible tube section 15 of the aforementioned insertion part 7 of the endoscope, between same and the tray, and a relatively large member 45, such as the operating section 8 or connector section 10 has been placed on top of the flexible tube section 15. When the endoscope, and the like, are introduced in this state into an autoclave sterilization device and autoclave sterilization is performed, there is a risk that, even in a room temperature environment after autoclave sterilization, a small indentation 47 may have formed in the portion of the flexible tube section 15 where the peripheral device 46 was touching same, as shown in FIG. 5B, due to thermal deformation.

Figure 5B:
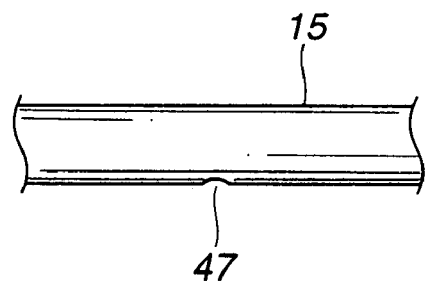
FIG. 5B is an external view showing a situation where a small indentation is formed by thermal deformation in the flexible tube section of the endoscope, when an endoscope is accommodated in a sterilization device, according to the prior art.

If the endoscope 2 is not introduced into the autoclave sterilization device, supposing that a state as shown in FIG. 5A arises, then although a small indentation may be formed in the flexible tube section 15 due to elastic deformation, this indentation 47 will not remain in the state in FIG. 5B where the state in FIG. 5A has been removed. However, since a high-temperature environment of 115° C.-138° C. is used in autoclave sterilization, as described above, then there is a risk that the indentation 47 will be formed as shown in FIG. 5B on the surface of the insertion part of the endoscope, even in a room temperature environment after autoclave sterilization, and if the indentation 47 is formed in this way, then both insertability characteristics or durability characteristics may decrease.

This is particularly important in the tip side of the flexible tube section 15 compared to the operator side thereof, and in an endoscope used for endoscopic examination of the lower digestive tract where the insertability characteristics and durability characteristics of the flexible tube section 15 are particularly influential, it is this first 70 cm portion (see FIG. 2) which is used in the case of practically all patients. Therefore, desirably, it should be devised that no local pressing forces are applied by other members to the flexible section in the portion up to at least 70 cm from the tip thereof.

In the present embodiment, a middle lid 36a is provided in such a manner that no local pressing force is applied to the outer surface of this portion, at the least, and hence deformation causing the aforementioned indentation 47, or the like, can be avoided, and furthermore, the occurrence of deformation causing indentations 47, or the like, in the surface of the universal cord 9 can also be prevented.

Since the aforementioned flexible tube section 15 has its own weight (gravitational force) acting against the lower face of the endoscope accommodating section 37, it does receive a reactive force corresponding to this weight, from the lower face of the endoscope accommodating section 37, but as the lower face of the endoscope accommodating section 37 is smooth and planar in shape, there is virtually no deformation of the surface of the flexible tube section 15 due to the effect of its own weight. Alternatively stated, this weight is not sufficient to generate deformation which presents an impediment of any kind.

Here, when a plurality of endoscopes are subjected to autoclave sterilization simultaneously, then if the autoclave sterilization device is relatively compact, the respective sterilization accommodating cases 34 may be introduced into the device in an overlapping fashion.

Conventionally, trays are mutually superposed in a state where the peripheral devices are overlapping with, or contacting, respective portions of the endoscope 2, and therefore pressing forces exceeding the weight of the respective portions of the endoscope 2 (weight per length unit) may act on these respective portions of the endoscope 2, and moreover, the contacting elements have a protruding shape, then there is a risk that local deformations such as the indentation 47 (caused by plastic deformation after high-temperature high-pressure steam sterilization) may arise in respective portion of the endoscope 2, in particular, in the surface of the flexible tube section 15.

In the present embodiment, by providing an outer lid 36b, no pressing force exceeding the weight of the respective portions of the endoscope, in particular, the flexible tube section 15 (weight per unit length), is caused to act inside the sterilization accommodating case 34.

Furthermore, in the present embodiment, the respective portions of the endoscope 2 are prevented from overlapping, and each element is constituted in such a manner that it generates no pressing forces, thereby yielding the beneficial effect that the steam is able to penetrate even into intimate regions thereof during autoclave sterilization.

Consequently, since no local plastic deformations remain on the surface of the insertion part of the endoscope, even after autoclave sterilization, it is possible to achieve a vessel for high-temperature high-pressure steam sterilization whereby no damage is caused to the insertion part of the endoscope by peripheral elements, when an endoscope capable of undergoing high-temperature high-pressure steam sterilization is subjected to autoclave sterilization.

Figure 6A:
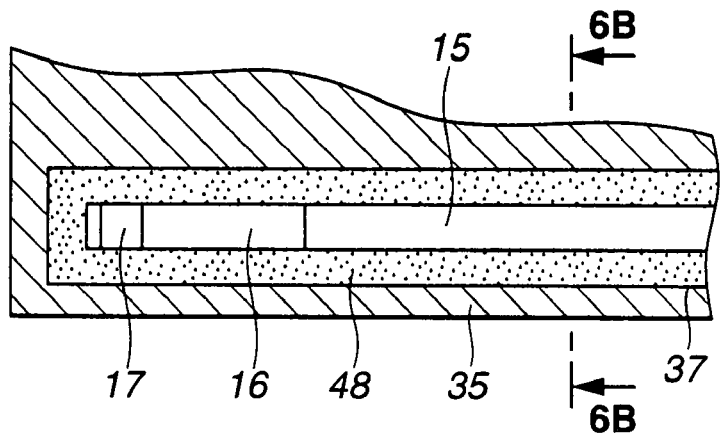
FIG. 6A is a sectional diagram showing a portion of a vessel for high-temperature high-pressure steam sterilization and the insertion part of an endoscope, in a case where the insertion part of the endoscope has been accommodated in a vessel for high-temperature high-pressure steam sterilization according to a second embodiment of the present invention.
Figure 6B:
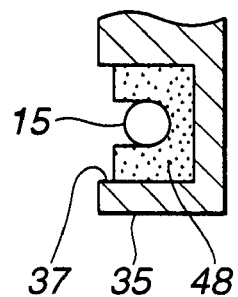
FIG. 6B is a sectional view showing a portion of a vessel for high-temperature high-pressure steam sterilization and the insertion part of an endoscope, in a case where the insertion part of the endoscope has been accommodated in a vessel for high-temperature high-pressure steam sterilization according to a second embodiment of the present invention.

Next, a second embodiment of the present invention is described referring to FIG. 6A and FIG. 6B.

FIG. 6A is a sectional diagram showing a portion of a vessel for high-temperature high-pressure steam sterilization and the insertion part of an endoscope, in a case where the insertion part of the endoscope has been accommodated in a vessel for high-temperature high-pressure steam sterilization according to a second embodiment of the present invention.

FIG. 6B is a sectional view showing a portion of a vessel for high-temperature high-pressure steam sterilization and the insertion part of an endoscope, in a case where the insertion part of the endoscope has been accommodated in a vessel for high-temperature high-pressure steam sterilization according to a second embodiment of the present invention.

In this second embodiment, the aforementioned endoscope accommodating section 37 is constituted by providing a flexible member with respect to the sterilization accommodating case 34 according to the first embodiment. The remaining composition is the same as the first embodiment, and therefore description thereof is omitted, and similar elements are labelled with the same numerals.

As shown in FIG. 6A, a flexible member 48 is provided in the endoscope accommodating section 37, in such a manner that the insertion part 7 of an endoscope can be accommodated in this flexible member 48. A composition is adopted wherein there is virtually no clearance between the flexible member 48 and the flexible tube section 15.

The flexible member 48 is a member made from a rubber or sponge having lower surface hardness than the surface of the flexible tube section 15, as shown in FIG. 6B, which is resistant to at least several high-temperature high-pressure steam sterilization operations.

By covering the region of the flexible tube section 15 by a flexible member 48 in this manner, and by using planar faces for the lower face and side faces, and the like, of the endoscope accommodating section 37 of the sterilization accommodating case according to the first embodiment, it is possible to reduce the pressing force applied to the surface of the flexible tube section 15. Moreover, by providing virtually no clearances, there is a very small possibility that another element will be inserted mistakenly into the endoscope accommodating section 37.

Consequently, since the surface of the flexible tube section 15 can be protected further by the sterilization accommodating case according to the first embodiment, it is possible to reduce the possibility of deformations after autoclave sterilization (high-temperature high-pressure steam sterilization).

Next, a third embodiment of the present invention is described referring to FIG. 7A, FIG. 7B, and FIG. 7C.

FIG. 7A is a sectional diagram showing a portion of a vessel for high-temperature high-pressure steam sterilization and the insertion part of an endoscope, in a case where the insertion part of the endoscope has been accommodated in a vessel for high-temperature high-pressure steam sterilization according to a third embodiment of the present invention.

FIG. 7B is a diagram showing a portion of the insertion part of the endoscope, in a case where the insertion part of the endoscope has been accommodated in a vessel for high-temperature high-pressure steam sterilization according to a third embodiment of the present invention.

FIG. 7C is a diagram showing a portion of the insertion part of the endoscope, in a case where the insertion part of the endoscope has been accommodated in a vessel for high-temperature high-pressure steam sterilization according to a third embodiment of the present invention.

FIG. 7B and FIG. 7A are diagrams showing a situation where a flexible tube section inside an over tube has been bent to too small a shape.

In this third embodiment, in contrast to the endoscope 2 according to the first embodiment, a protective tube capable of undergoing high-temperature high-pressure steam sterilization having a larger internal diameter than the external form of the insertion part of the endoscope is attached to the flexible tube section 15, separately from the sterilization accommodating case, and in this state, the endoscope 2 is accommodated in a tray 35. The remainder of the composition is the same as the first embodiment, and hence description thereof is omitted here, and similar compositional elements are labelled with the same numerals.

As shown in FIG. 7A, an over tube 49 forming a protective tube capable of undergoing high-temperature high-pressure steam sterilization having a larger internal diameter than the external form of the flexible tube section 15 is placed over the flexible tube section 15 of the insertion part of the endoscope, and in this state, the endoscope 2 is accommodated in the tray 35.

The internal diameter of the over tube 49 is set to be greater than the external diameter of the flexible tube section 15 in such a manner that a clearance is provided therebetween, and it is made from an elastic and sufficiently flexible material. A flange section 50 is provided on a portion of the over tube 49, and by means of this flange section 50 engaging with a predetermined portion of the side of the tray 35, the over tube 49 is prevented from moving (sliding) significantly with respect to the flexible tube section 15.

As shown in FIG. 7B, supposing that the flexible tube section 15 inside the over tube 49 is bent too small (although tube section 15 does not actually buckle), since the outer circumference side of the flexible tube section 15 is stretched and the inner circumference side thereof is contracted, wrinkles will occur.

Here, supposing a case where wrinkles 51 form as shown in FIG. 7B, but the endoscope 2 is not introduced into the autoclave sterilization (high-temperature high-pressure steam sterilization) device, there is a possibility that such bending may occur due to elastic deformation during medical examination, and the like, and therefore, when the bending is released, the wrinkles 51 will disappear, and not cause a problem, but if introduced into the autoclave sterilization device and subjected to autoclave sterilization, the shape of the wrinkles 51 will remain on the surface of the flexible tube section 15 due to thermal deformation, and this may have a detrimental effect on the insertability and durability characteristics of the flexible tube section 15.

In the present embodiment, the flexible tube section 15 is bent to a bending radius which does not generate wrinkles 51 of this kind. Thereby, in the present embodiment, (as described in common in the other embodiments), the bending radius formed when the flexible tube section 15 is bent and accommodated is designed to assume a predetermined bending shape which does not generate wrinkles 51.

As shown in FIG. 7C, there is sufficient clearance between the flexible tube section 15 and the internal diameter of the over tube 49, in such a manner that the surface of the flexible tube section 15 is received by the concave surface of the over tube 49.

By placing an over tube 49 having the foregoing composition over the flexible tube section 15, then even supposing that the accommodating section for the surgical instrument 43, rinsing tool 44, and the like, is not separated from the accommodating section for the endoscope 2, the surgical instrument 43 and rinsing tool 44 will not press against the surface of the flexible tube section 15. Moreover, even if the connector section 10 of the endoscope 2 is not fixed to a predetermined position, the connection section 10 will not overlap with (ride up onto) the surface of the flexible tube section 15.

In this way, greater freedom of accommodation is achieved. Moreover, since the face confronting the surface of the flexible tube section 15 is the concave face of the interior of the over tube 49, rather than a flat surface, there is a lighter contact on the surface of the flexible tube section 15 than is the case with a flat surface.

As a result, it is possible to increase freedom of accommodation and to protect the portions of the endoscope 2 that are to be protected, with greater reliability, compared to the sterilization accommodating cases of the first and second embodiments.

Next, a fourth embodiment of the invention is described referring to FIG. 8, FIG. 9A, FIG. 9B and FIG. 9C.

Figure 8:
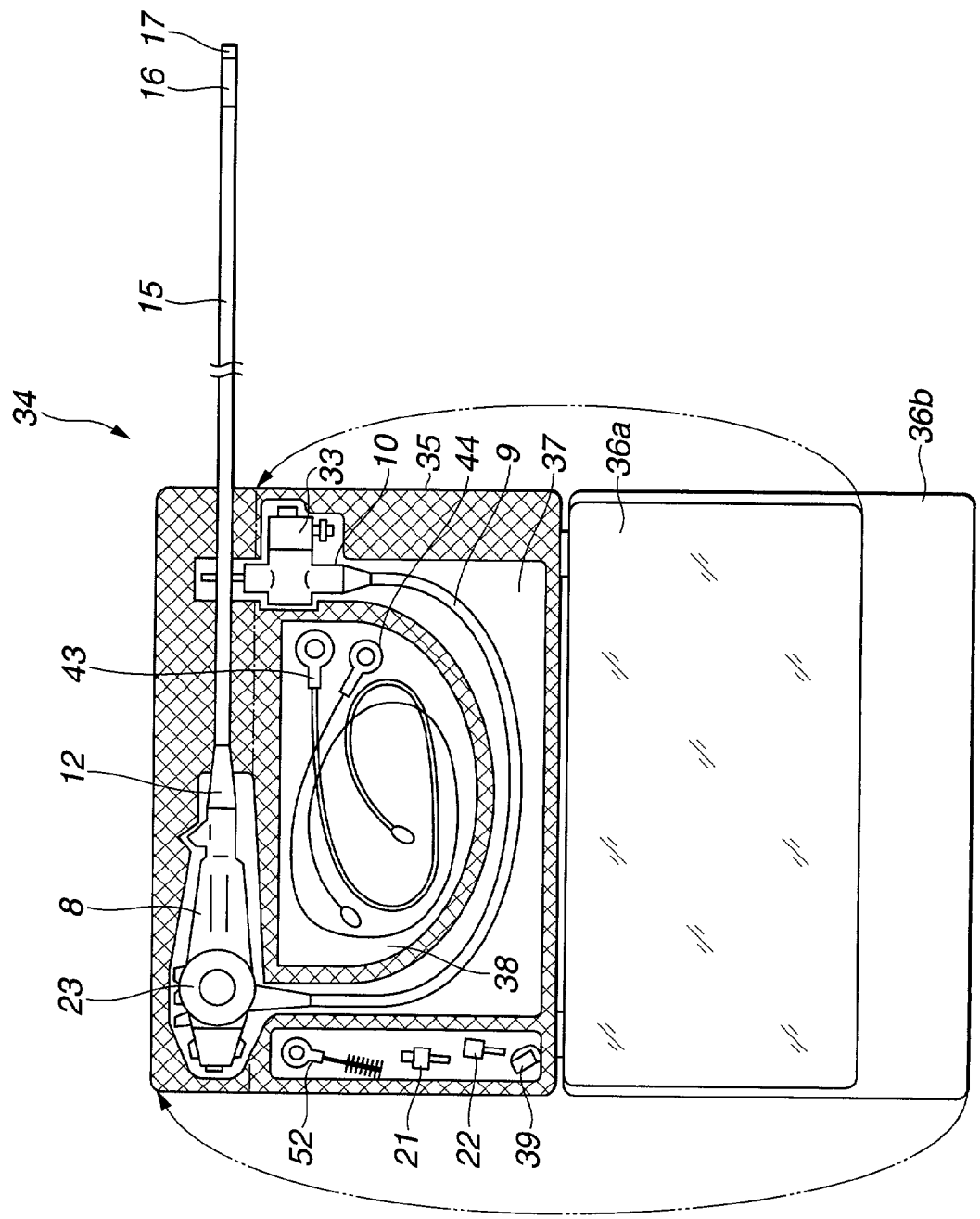
FIG. 8 is a plan view of a state where an endoscope is accommodated in a vessel for high-temperature high-pressure steam sterilization according to a fourth embodiment, showing a situation where both a middle lid and an outer lid of the vessel for high-temperature high-pressure steam sterilization are opened.

FIG. 8 is a plan view of a state where an endoscope is accommodated in a vessel for high-temperature high-pressure steam sterilization according to a fourth embodiment, showing a situation where both a middle lid and an outer lid of the vessel for high-temperature high-pressure steam sterilization are opened.

Figure 9A:
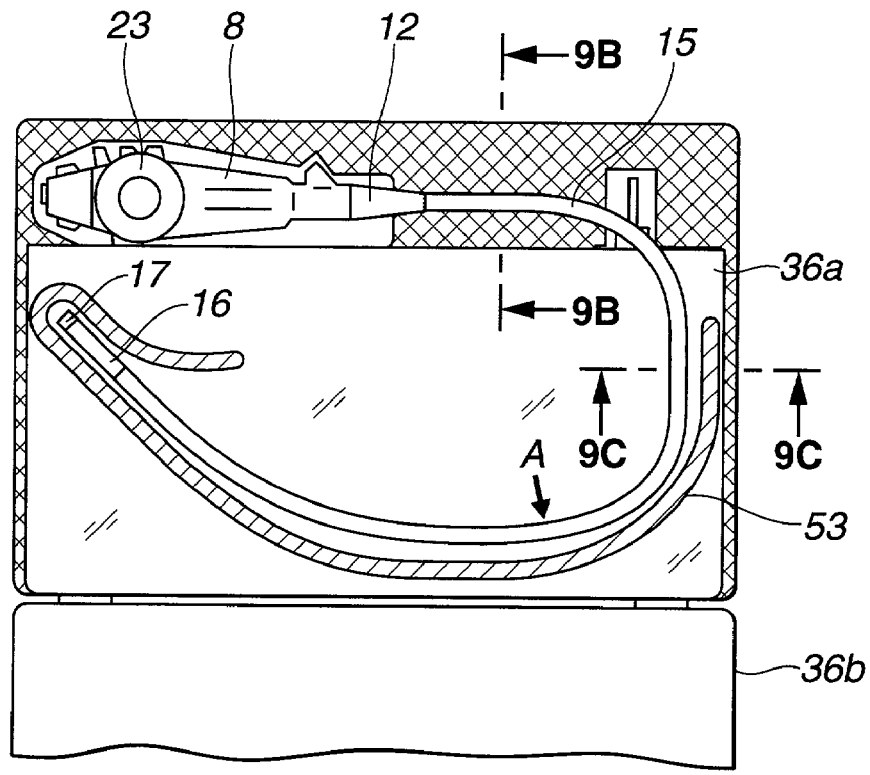
FIG. 9A is a plan view of a state where an endoscope is accommodated in a vessel for high-temperature high-pressure steam sterilization according to a fourth embodiment, showing a situation where the middle lid of the vessel for high-temperature high-pressure steam sterilization is closed.

FIG. 9A is a plan view of a state where an endoscope is accommodated in a vessel for high-temperature high-pressure steam sterilization according to a fourth embodiment, showing a situation where the middle lid of the vessel for high-temperature high-pressure steam sterilization is closed.

Figure 9B:
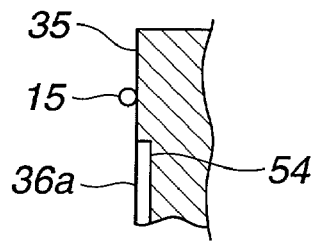
FIG. 9B is a sectional diagram showing the vessel for high-temperature high-pressure steam sterilization and the endoscope, with a part thereof being cut away, in a state where a middle lid of the vessel for high-temperature high-pressure steam sterilization is closed after accommodating an endoscope in a vessel for high-temperature high-pressure steam sterilization according to the fourth embodiment.

FIG. 9B is a sectional diagram showing a state where a middle lid of the vessel for high-temperature high-pressure steam sterilization is closed after accommodating an endoscope in a vessel for high-temperature high-pressure steam sterilization according to the fourth embodiment, while cutting away a portion of the vessel for high-temperature high-pressure steam sterilization and the endoscope.

Figure 9C:
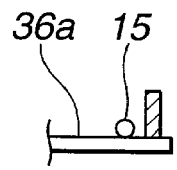
FIG. 9C is a sectional diagram showing the vessel for high-temperature high-pressure steam sterilization and the endoscope, with a part thereon being cut away, in a state where a middle lid of the vessel for high-temperature high-pressure steam sterilization is closed after accommodating an endoscope in a vessel for high-temperature high-pressure steam sterilization according to the fourth embodiment.

FIG. 9C is a sectional diagram showing a state where a middle lid of the vessel for high-temperature high-pressure steam sterilization is closed after accommodating an endoscope in a vessel for high-temperature high-pressure steam sterilization according to the fourth embodiment, showing a cutaway portion of the vessel for high-temperature high-pressure steam sterilization and the endoscope.

In the first to third embodiments, a sterilization accommodating case is constituted in such a manner that the insertion part 15 of the endoscope, including the distal end section 17, is accommodated inside an endoscope accommodating section 37 formed in a tray 35, but in the fourth embodiment, a composition is adopted whereby the distal end section 17, from an intermediate point of the flexible tube section of the insertion part of the endoscope, may be accommodated in an accommodating section provided in the middle lid. With this exception, the composition is the same as the first embodiment, and description thereof is omitted here and similar compositional elements are labelled with the same numerals.

FIG. 8 shows an intermediate stage of accommodating an endoscope 2 in the tray 35, wherein the operating part 8, universal cord 9, connector part 10 and waterproof cap 33 have been accommodated in a predetermined position (endoscope accommodating section 37) of the tray 35, but in this fourth embodiment, the flexible tube section 15 is not accommodated inside the tray 35 (inside the endoscope accommodating section 37).

The middle lid 36a closes up to the portion of the tray 35 as indicated by the single-dotted line, and the height of the shaded portion of the tray 35 is formed to have a greater height than the connector part 10 when the middle lid 36a is closed over this portion of the tray 35 indicated by the single-dotted line, and hence the universal cord 9 and connector part 10 can be positioned and accommodated therein within a certain amount of clearance, in such a manner that they do not contact any elements other than the tray 35 or the middle lid 36a.

If the middle lid 36a is closed from the state in FIG. 8 and the flexible tube section 15 of the insertion part of the endoscope is accommodated on the middle lid 36a, then as shown in FIG. 9A, the flexible tube section 15 is positioned along a curved wall 53 provided on the upper face of the middle lid 36a.

As shown in FIG. 9B, the middle lid 36a closes into a step section 54 of the tray 35, and hence there is no overlapping of the upper face of the tray 35 and the middle lid 36a and the upper face of the tray 35 has an approximately uniform flat surface. In other words, the flexible tube section 15 can be positioned in such a manner that it does not form a protruding section, or the like, on the middle tray 36a, over the tray 35.

As shown in FIG. 9C, the height of the curved wall 53 is set to a greater height than the diameter of the flexible tube section 15, and therefore, the outer lid 36b never presses against the flexible tube section 15, even when the outer lid 36b is closed.

In this way, although the flexible tube section 15 overlaps with the universal cord 9 and connector section 10 in terms of three-dimensional positions, it is separated therefrom by the middle lid 36a.

Here, in the first to third embodiments, a layout was adopted wherein the universal cord 9, flexible tube section 15, and the like, were accommodated towards the inside, in order to prevent the flexible tube section 15 from being pressed by other portions of the endoscope 2, whilst also aiming to achieve compact accommodation of elements, and avoiding bending the flexible tube section 15 to a small shape, as far as possible.

In this case, there is a risk that the universal cord 9 may be bent to a small shape, and that notable bending kinks may occur in the universal cord 9. However, in the fourth embodiment, although the tray 35 is the same size as that in the first to third embodiments, the flexible tube section 15 and universal cord 9 are separated, respectively being positioned above and below the middle tray 36a, and therefore, both the flexible tube section 15 and the universal cord 9 can be accommodated in a loose bending shape.

In the fourth embodiment, similarly to the first embodiment, the 70 cm portion from the tip until the arrow A has a very loose bending shape, and the portion from this 70 cm portion until the operator side forms a tighter bending radius. In this way, if the flexible tube section 15 must be bent to be accommodated, then by taking 70 cm as a reference point, and changing the bending shape between the portion up to the 70 cm point marked by arrow A, and the portion thereafter until the operator side, it is possible to maintain very high-level characteristics in the flexible tube section 15, even if bending kinks are formed in the flexible tube section 15 after autoclave sterilization.

Consequently, since the universal cord 9 and the flexible tube section 15 can be accommodated in a looser bending shape than in the first to third embodiments, it is possible to reduce further the effects of bending kinds, and the like, on both the universal cord 9 and the flexible tube section 15, after autoclave sterilization.

The present invention is not limited to the embodiments described above, and may also be implemented by making various modifications, without departing from the essence of the invention.

According to the present invention described above, it is possible to achieve a vessel for high-temperature high-pressure steam sterilization whereby, when an endoscope capable of undergoing high-temperature high-pressure steam sterilization is subjected to autoclave sterilization, the insertion part of the endoscope is not damaged by any peripheral elements.

Having described the preferred embodiments of the invention referring to the accompanying drawings, it is to be understood that the invention is not limited to those precise embodiments and that various changes and modifications thereof could be effected by one skilled in the art without departing from the spirit or scope of the invention as defined in the appended claims.

What is claimed is:

1. A vessel for high-temperature high-pressure steam sterilization for accommodating an endoscope having a flexible inserting portion and an integral operating portion and for performing high-temperature high-pressure steam sterilization, the vessel comprising:
   a tray having a first accommodating section in which the operating portion can be positioned and accommodated;
   a lid member which can be selectively set in a closed state to cover at least a part of the first accommodating section and in an open state to expose the first accommodating section as a whole with respect to the tray, the lid member having a second accommodating section capable of accommodating the flexible inserting portion;
   wherein the second accommodating section is provided in the surface of the lid member that is on a reverse side of a surface opposing the first accommodating section when the lid member is in the closed state to cover the first accommodating section.

2. The vessel for high-temperature high-pressure steam sterilization according to claim 1, further comprising:
   an outer lid member to cover the second accommodating section of the lid member which is set in the closed state with respect to the tray.

3. The vessel for high-temperature high-pressure steam sterilization according to claim 1, wherein the lid member has a positioning portion to accommodate the flexible inserting portion so that portions of the flexible insertion portion do not come into contact with each other.

4. The vessel for high-temperature high-pressure steam sterilization according to claim 1, wherein the flexible inserting portion-integral with the operating portion that is accommodated in the first accommodating section provided in the tray and the second accommodating section is adapted to accommodate a middle portion of the flexible inserting portion.

5. A vessel for high-temperature high-pressure steam sterilization for accommodating an endoscope having a flexible inserting portion and an integral operating portion and for performing high-temperature high-pressure steam sterilization, the vessel comprising:
   a first accommodating member that is a tray in which the operating portion can be positioned and accommodated; and
   a second accommodating member rotatably disposed on the first accommodating member, the second accommodating member being adapted to accommodate the flexible inserting portion to prevent at least one of the flexible inserting portion from coming into direct contact with the operating portion and surfaces of portions of the flexible inserting portion from coming into direct contact with each other in a state of having accommodated the operating portion in the first accommodating member, wherein the first accommodating member is separate from the second accommodating member.

6. The vessel for high-temperature high-pressure steam sterilization according to claim 5, wherein the second accommodating member is a lid member which can be selectively arranged in a closed state to cover at least a part of the first accommodating member and in an open state to show the first accommodating member as a whole with respect to the first accommodating member.

7. The vessel for high-temperature high high-pressure steam sterilization according to claim 6, wherein the lid member has a curved wall in order to accommodate the flexible inserting portion with a curved shape.

8. The vessel for high-temperature high-pressure steam sterilization according to claim 7, wherein the lid member has a surface opposing the first accommodating member when the lid member covers the first accommodating member and an opposing surface, and the curved wall is provided on the opposing surface.

9. The vessel for high-temperature high-pressure steam sterilization according to claim 6, wherein the lid member is adapted to accommodate a portion of the flexible inserting portion from a distal end of the flexible inserting portion to a portion between the distal end and a proximal end of the flexible inserting portion.

10. A vessel for high-temperature high-pressure steam sterilization for accommodating an endoscope having a flexible inserting portion and an integral operating portion and for performing high-temperature high-pressure steam sterilization, the vessel comprising:
  a first accommodating member that is a tray in which the operating portion can be positioned and accommodated;
  a second accommodating member rotatably disposed on the first accommodating member, the second accommodating member being adapted to accommodate the flexible inserting portion to prevent at least one of the flexible inserting portion from coming into direct contact with the operating portion and surfaces of portions of the flexible inserting portion from coming into direct contact with each other in a state of having accommodated the operating portion in the first accommodating member, wherein the first accommodating member is separate from the second accommodating member, wherein the second accommodating member is a lid member which can be selectively arranged in a closed state to cover at least a part of the first accommodating member and in an open state to show the first accommodating member as a whole with respect to the first accommodating member; and
  an outer lid member which covers the lid member arranged in the closed state with respect to the first accommodating member.

11. A vessel for high-temperature high-pressure steam sterilization for accommodating an endoscope having a flexible inserting portion and an integral operating portion and for performing high-temperature high-pressure steam sterilization, the vessel comprising:
  a tray having a first accommodating section in which the operating portion can be positioned and accommodated;
  a lid member which can be selectively set in a closed state to cover at least a part of the first accommodating section and in an open state to expose the first accommodating section as a whole with respect to the tray, the lid member having a second accommodating section capable of accommodating the flexible inserting portion; and
  an outer lid member to cover the second accommodating section of the lid member which is set in the closed state with respect to the tray.

* * * * *